(12) United States Patent
Park et al.

(10) Patent No.: US 9,366,646 B2
(45) Date of Patent: Jun. 14, 2016

(54) HYDROGEN MEASUREMENT SENSOR HAVING JUNCTION STRUCTURE OF SOLID OXYGEN ION CONDUCTOR AND SOLID HYDROGEN ION CONDUCTOR IN MOLTEN METAL

(71) Applicant: KOREA ADVANCED INSTITUTE OF SCIENCE AND TECHNOLOGY, Daejeon (KR)

(72) Inventors: Chong Ook Park, Daejeon (KR); Byoung Hyo Jung, Daejeon (KR)

(73) Assignee: KOREA ADVANCED INSTITUTE OF SCIENCE AND TECHNOLOGY (KR)

( * ) Notice: Subject to any disclaimer, the term of this patent is extended or adjusted under 35 U.S.C. 154(b) by 0 days.

(21) Appl. No.: 14/382,606

(22) PCT Filed: Dec. 6, 2012

(86) PCT No.: PCT/KR2012/010502
§ 371 (c)(1),
(2) Date: Sep. 3, 2014

(87) PCT Pub. No.: WO2013/137543
PCT Pub. Date: Sep. 19, 2013

(65) Prior Publication Data
US 2015/0021181 A1    Jan. 22, 2015

(30) Foreign Application Priority Data

Mar. 14, 2012  (KR) .................. 10-2012-0025979

(51) Int. Cl.
*G01N 27/407* (2006.01)
*G01N 27/411* (2006.01)
*G01N 33/20* (2006.01)

(52) U.S. Cl.
CPC ........ *G01N 27/4074* (2013.01); *G01N 27/4112* (2013.01); *G01N 27/4114* (2013.01); *G01N 33/206* (2013.01)

(58) Field of Classification Search
CPC ........... G01N 27/411–27/4115; G01N 27/407; G01N 27/4071; G01N 27/4073; G01N 27/4074; G01N 33/05
See application file for complete search history.

(56) References Cited

U.S. PATENT DOCUMENTS 7,396,443 B2    7/2008   Park et al.

FOREIGN PATENT DOCUMENTS

JP        10123093       5/1998
JP    2000-19152 A  *  1/2000  ........... G01N 27/416
(Continued)

OTHER PUBLICATIONS

JPO computer-generated English language translation of Katahira et al. JP 2000-19152 A, patent published Jan. 21, 2000.*

(Continued)

*Primary Examiner* — Alexander Noguerola
(74) *Attorney, Agent, or Firm* — Cantor Colburn LLP (57) ABSTRACT

Provided is a hydrogen measurement sensor capable of monitoring a content of hydrogen within molten metal in real-time using an aluminum or magnesium alloy casting method, and, more particularly, a hydrogen measurement sensor having a junction structure of a solid oxygen ion conductor and a solid hydrogen ion conductor in molten metal capable of measuring a content of hydrogen within aluminum-magnesium alloy-molten metal using a new method which generates a fixed concentration of oxygen gas from a solid reference material at a high temperature by replacing a reference material of a standard gas method which is difficult to handle with a solid reference material or external air which is easy to handle or has the same effect as that of the gas reference material by using a feature in which the external air contains a predetermined pressure (0.21 atm) of oxygen.

8 Claims, 5 Drawing Sheets

(56) References Cited

FOREIGN PATENT DOCUMENTS

| JP | 2000-88794 A | * | 3/2000 | ........... G01N 27/406 |
|----|--------------|---|--------|--------------------------|
| JP | 2002202281 | | 7/2002 | |
| KR | 2019840001154 | | 6/1984 | |
| KR | 1020040067752 | | 7/2004 | |
| KR | 100499044 | | 6/2005 | |
| KR | 1020060025079 | | 3/2006 | |
| WO | 2004025289 | | 3/2004 | |

OTHER PUBLICATIONS

JPO computer-generated English language translation of Katahira et al. JP 2000-88794 A, patent published Mar. 31, 2000.*

JPO computer-generated English language translation of Hibino et al. JP 2002-202281 A, patent published Jul. 19, 2002.*

International Search Report—PCT/KR2012/010502 dated Mar. 28, 2013.

European Search Report—European Application No. 12871533.1 issued on Oct. 20, 2015, citing Lu, et al., JP 2002 202281, JP 2000 088794, WO 2004/025289 and Korotcenkov, et al.

Jiang, et al., Inorganic nonmetal material manual, Beijing: Chemical Industry Press, 2009, pp. 386-388.

Korotcenkov, et al., Review of Electrochemical Hydrogen Sensors, Chemical Reviews, 2009, pp. 1402-1433.

Lu, et al., High-temperature hydrogen sensor based on stabilized zirconia and a metal oxide electrode, Sensors and Actuators, 1996, pp. 130-135.

Qu, Modern ceramic material and technology, Shanghai: EastChina University of Science and Technology Press, 2008, p. 209.

* cited by examiner

FIG. 5

HYDROGEN MEASUREMENT SENSOR HAVING JUNCTION STRUCTURE OF SOLID OXYGEN ION CONDUCTOR AND SOLID HYDROGEN ION CONDUCTOR IN MOLTEN METAL

TECHNICAL FIELD

The present invention relates to a hydrogen measurement sensor capable of monitoring a content of hydrogen within molten metal in real-time using an aluminum or magnesium alloy casting method, and more particularly, to a hydrogen measurement sensor having a junction structure of a solid oxygen ion conductor and a solid hydrogen ion conductor in molten metal capable of measuring a content of hydrogen within aluminum-magnesium alloy-molten metal using a new method which generates a fixed concentration of oxygen gas from a solid reference material at a high temperature by replacing a reference material of a standard gas method which is difficult to handle with a solid reference material or external air which is easy to handle or has the same effect as that of the gas reference material by using a feature in which the external air contains a predetermined pressure (about 0.21 atm) of oxygen.

BACKGROUND ART

Generally, as a method for producing products in aluminum or magnesium industries, there are various methods such as a casting method for making a desired shape by melting metal and a method for mixing and sintering powder type raw materials. A high temperature melting casting technology is most frequently used in the method. However, one of the main factors of determining a quality of products in the aluminum or magnesium casting process is an amount of dissolved hydrogen which is generated by penetrating moisture decomposed in the atmosphere into molten metal. Since the dissolved hydrogen has a difference in solubility of about 10 to 20 times in a liquid state and a solid state, the hydrogen is agglomerated at the time of coagulation of a molten aluminum-magnesium alloy and thus pores are formed. These pores not only degrade strength of products but also damage appearance, which is emerging as an important issue in the aluminum or magnesium industries. To solve the problem, a degassing process of forcibly extracting the hydrogen within the molten metal using argon or chloride gas has been carried out in the industrial site. However, the degassing process has a considerable difficulty in making products having a constant content of hydrogen since time required for the degassing process is changed due to the surrounding environment in which the molten metal is melted, a content of impurities within the molten metal, and weather effects of humidity, temperature, or the like. Therefore, a need exists for a development of a hydrogen sensor which may control a quality of molten metal with a constant content of hydrogen by monitoring the content of hydrogen within the molten metal in real time, independent of the surrounding factors.

However, a technology which is mainly used to measure the content of hydrogen within the molten metal in producing the aluminum or magnesium products uses a method for cutting the product coming out after coagulating the molten metal and observing pores within the product to calculate the content of hydrogen; however, for the measurement of the content of hydrogen based on the method, may not avoid a breakage of a final product.

Further, another method uses a hydrogen sensor which measures the content of hydrogen within the aluminum or magnesium molten metal and uses only a hydrogen ion solid electrolyte and therefore blows gas having a standard hydrogen concentration into one surface of an electrode (reference electrode) to fix a hydrogen concentration of the reference electrode and putting the other surface of the electrode into the molten metal to measure an electromotive force generated due to a difference between a hydrogen partial pressure within the molten metal and a hydrogen pressure of the standard gas, thereby measuring the content of hydrogen within the molten metal. However, due to the standard hydrogen gas of the reference electrode used to fix the hydrogen partial pressure, a gas barrel is accompanied at all time at the time of the measurement and therefore the measurement apparatus becomes huge and a gas demand is continuously generated, such that the inconvenience of measurement and the problem of costs and safety due to transportation and frequent replacement of the reference hydrogen gas barrel occur.

Figure 1:
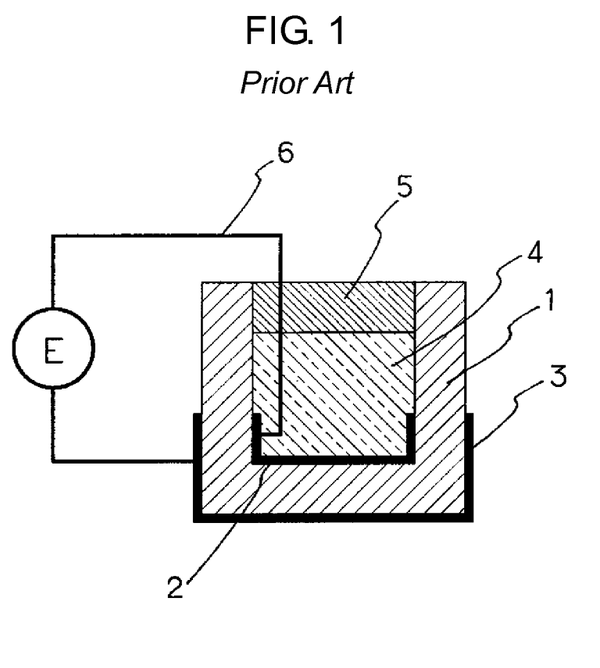
FIG. 1 is a schematic diagram illustrating a hydrogen sensor according to the related art.

Further, to solve the problem, as illustrated in FIG. 1, there is a hydrogen sensor for aluminum (alloy) molten metal (Korean Patent No. 10-0499044) configured to include a hydrogen ion conductor 1, a solid reference material 4 filled in the hydrogen ion conductor 1, a ceramic cover 5 formed on the solid reference material, a reference electrode 2 formed between the solid reference material 4 and the hydrogen ion conductor 1, a measurement electrode 3 formed outside the hydrogen ion conductor 1, and a wire 6 connecting the reference electrode 2 to the measurement electrode 3. The hydrogen sensor for aluminum molten metal may be configured to measure the concentration of hydrogen by fixing the hydrogen partial pressure of hydrogen which becomes a reference using $Ti/TiH_2/TiO$, $Ca/CaH_2/CaO$, or the like which is the solid reference material 4 but requires a high temperature sealing technology of sealing gas at a high temperature and therefore may cause a problem of making a structure of packaging complex.

RELATED ART DOCUMENT

Patent Document

KR 10-0499044 B1 (Jun. 23, 2005)

DISCLOSURE

Technical Problem

An object of the present invention is to provide a hydrogen measurement sensor having a junction structure of a solid oxygen ion conductor and a solid hydrogen ion conductor in molten metal based on a new method capable of monitoring a content of dissolved hydrogen within the molten metal in real-time to control the content of hydrogen within the molten metal which dominates a quality of products at the time of producing a casting products of an aluminum-magnesium alloy and generating a fixed concentration of oxygen gas from a solid reference material at a high temperature by replacing a reference material of a standard gas method which is difficult to handle with a solid reference material or external air which is easy to handle or having the same effect as that of the gas reference material by using a feature in which the external air contains a predetermined pressure (0.21 atm) of oxygen.

Technical Solution

In one general aspect, a hydrogen measurement sensor having a junction structure of a solid oxygen ion conductor and a solid hydrogen ion conductor in molten metal, includes an oxygen ion conductor 100 whose inside is hollow and one portion is open; a hydrogen ion conductor 200 coupled with an outer side of the oxygen ion conductor 100; a measurement metal electrode 300 formed at an outer side of the hydrogen ion conductor 200; a reference metal electrode 400 formed inside the oxygen ion conductor 100; and voltage measurement wires 600 connected to the measurement metal electrode 300 and the reference metal electrode 400, respectively.

The oxygen ion conductor 100 may be made of a solid electrolyte including zirconia $ZrO_2$ or any one selected from materials in which $GdO_3$ is added to $CeO_2$-based materials.

The zirconia $ZrO_2$ may be any one selected from yttria stabilized zirconia (YSZ), calcium stabilized zirconia (CSZ), and magnesium stabilized zirconia (MSZ).

The hydrogen ion conductor 200 may be made of any one selected from $CaZrO_3$-based compounds including $CaZr_{0.9}In_{0.1}O_{3-X}$, $SrZrO_3$-based compounds including $SrZr_{0.95}Y_{0.05}O_{3-X}$, $SrCeO_3$-based compounds including $SrCe_{0.95}Yb_{0.05}O_{3-X}$, and $BaCeO_3$-based compounds including $BaCe_{0.9}Nd_{0.1}O_{3-X}$ as a compound in which other materials are substituted into place B of a material having an $ABO_3$ type perovskite structure or any one selected from Ti-based compounds including $BaTiO_3$, $SrTiO_3$, or $PbTiO_3$.

The hydrogen measurement sensor may further include: a ceramic tube 700 which is coupled with an upper portion of the hydrogen ion conductor 200 and has both sides opened.

Advantageous Effects

According to the exemplary embodiments of the present invention, the hydrogen measurement sensor having a junction structure of a solid oxygen ion conductor and a solid hydrogen ion conductor in molten metal replaces the reference material of the standard gas method which is difficult to handle with the solid reference material or the external air which is easy to handle to obtain the same effect as that of the gas reference material, thereby simplifying the measurement apparatus.

Further, the hydrogen gas barrel is not required and thus the costs may be saved and the safety may be improved.

In addition, the content of hydrogen within the molten metal may be accurately measured and thus the quality of the final aluminum or magnesium product may be improved and the high reproducibility may be made in the manufacturing process.

DETAILED DESCRIPTION OF MAIN ELEMENTS

1000: (The Inventive) Hydrogen measurement sensor
100: Oxygen ion conductor

200: Hydrogen ion conductor
300: Measurement metal electrode
400: Reference metal electrode
500: Air
600, 610, 620: Voltage measurement wire
700: Ceramic tube
800: Molten metal

BEST MODE

Hereinafter, a hydrogen measurement sensor having a junction structure of a solid oxygen ion conductor and a solid hydrogen ion conductor in molten metal according to exemplary embodiments of the present invention will be described in detail with reference to the accompanying drawings.

Figure 2:
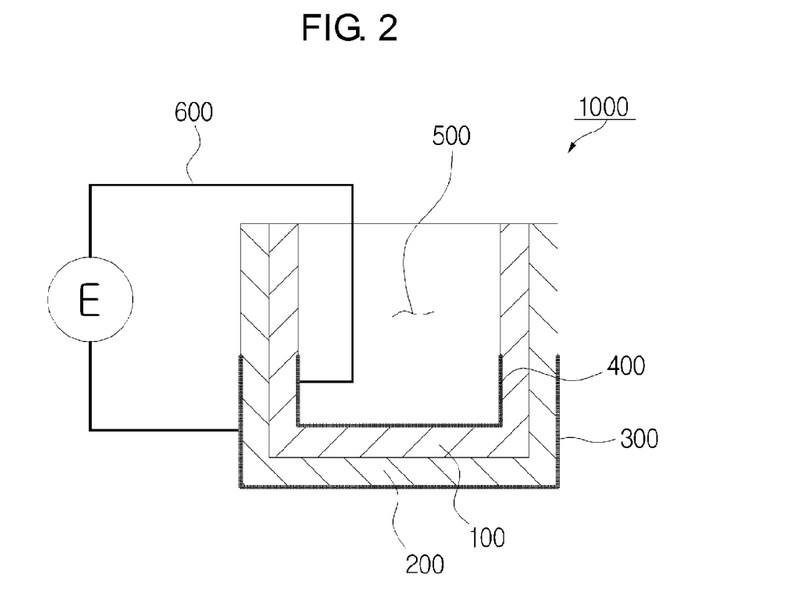
FIG. 2 is a cross-sectional view schematically illustrating a hydrogen measurement sensor according to an exemplary embodiment of the present invention.
Figure 3:
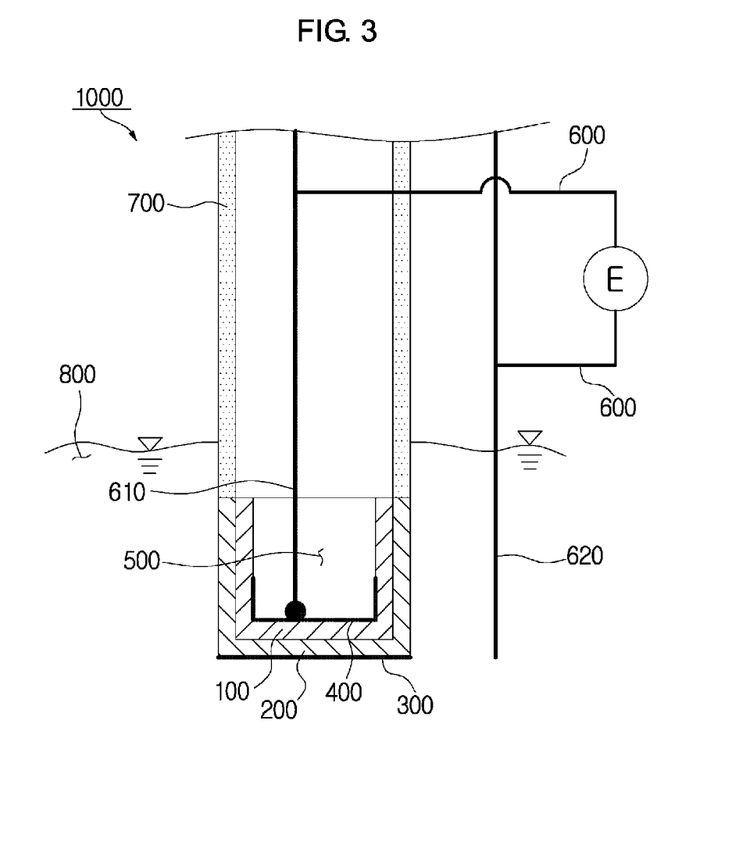
FIG. 3 is a cross-sectional view schematically illustrating a state in which the hydrogen measurement sensor according to the exemplary embodiment of the present invention is equipped within molten metal.
Figure 4:
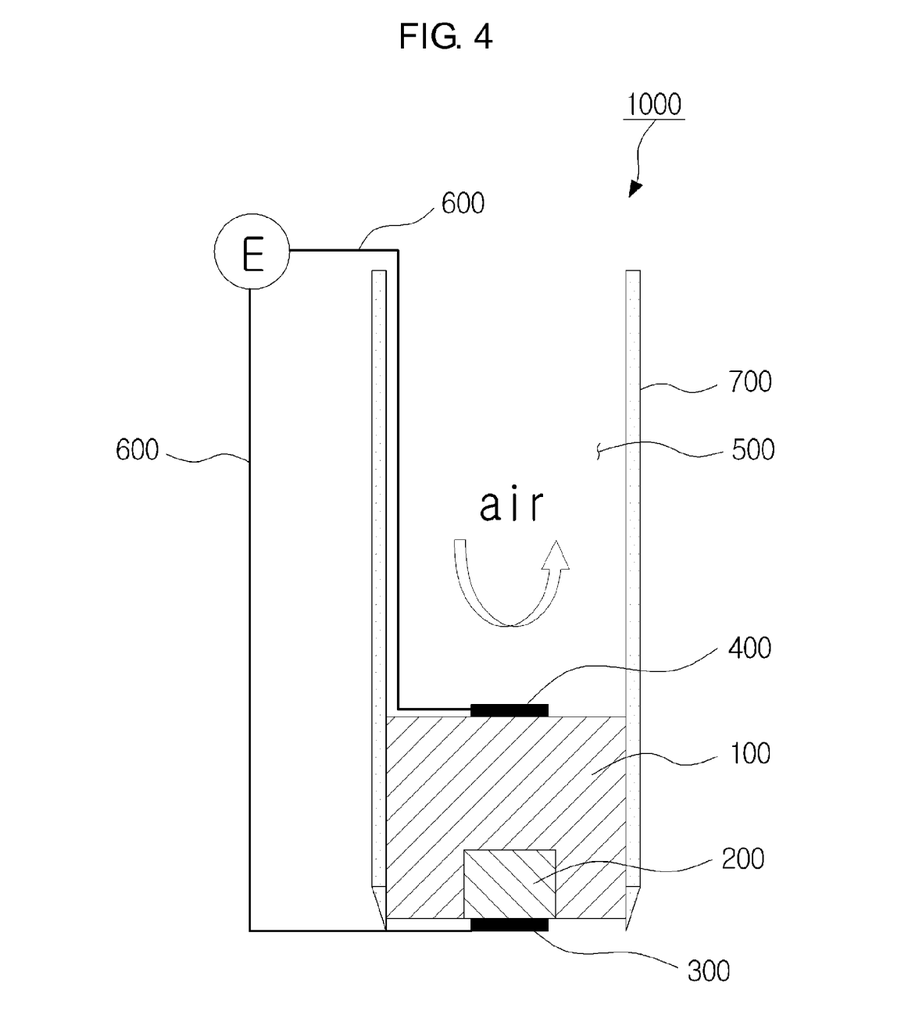
FIG. 4 is a cross-sectional view schematically illustrating a hydrogen measurement sensor according to another exemplary embodiment of the present invention.

FIG. 2 is a cross-sectional view schematically illustrating a hydrogen measurement sensor having a junction structure of a solid oxygen ion conductor and a solid hydrogen ion conductor in molten metal according to an exemplary embodiment of the present invention. FIG. 3 is a diagram illustrating an application example in which an oxygen ion conductor and a hydrogen ion conductor have a tube type and FIG. 4 is a diagram illustrating an application structure in which the hydrogen ion conductor is buried into the oxygen ion conductor in a pellet form.

As illustrated, the hydrogen measurement sensor having a junction structure of a solid oxygen ion conductor and a solid hydrogen ion conductor in molten metal according to the exemplary embodiment of the present invention is configured to include: an oxygen ion conductor 100 whose inside is hollow and one portion is open; a hydrogen ion conductor 200 coupled with an outer side of the oxygen ion conductor 100; a measurement metal electrode 300 formed at an outer side of the hydrogen ion conductor 200; a reference metal electrode 400 formed inside the oxygen ion conductor 100; and voltage measurement wires 600 connected to the measurement metal electrode 300 and the reference metal electrode 400, respectively.

First, the oxygen ion conductor 100 has a cup form in which an inside is hollow, a lower portion stops, and an upper portion is open. In this case, the oxygen ion conductor 100 may be made of a solid electrolyte including zirconia $ZrO_2$ or any one selected from materials in which $GdO_2$ is added to $CeO_2$-based materials. Further, the zirconia $ZrO_2$ may be any one selected from yttria stabilized zirconia (YSZ), calcium stabilized zirconia (CSZ), and magnesium stabilized zirconia (MSZ).

Further, the hydrogen ion conductor 200 is coupled with the outer side of the oxygen ion conductor 100. That is, the hydrogen ion conductor 200 also has a cup form and is thus formed to have the opened upper portion by having the oxygen ion conductor 100 foldably coupled with the inner side thereof. In this case, the hydrogen ion conductor 200 may be made of any one selected from $CaZrO_3$-based compounds including $CaZr_{0.9}In_{0.1}O_{3-X}$, $SrZrO_3$-based compounds including $SrZr_{0.95}Y_{0.05}O_{3-X}$, $SrCeO_3$-based compounds including $SrCe_{0.95}Yb_{0.05}O_{3-X}$, and $BaCeO_3$-based compounds including $BaCe_{0.9}Nd_{0.1}O_{3-X}$ as a compound in which other materials are substituted into place B of a material having an $ABO_3$ type perovskite structure or any one selected from Ti-based compounds including $BaTiO_3$, $SrTiO_3$, or $PbTiO_3$.

In this case, the oxygen ion conductor 100 and the hydrogen ion conductor 200 may be formed to have the same thickness and a thickness of each portion thereof may be formed uniformly.

Here, the measurement metal electrode 300 may be formed at the outer side of the hydrogen ion conductor 200 and the measurement metal electrode 300 may be formed at a lower end or a side of the hydrogen ion conductor 200.

Further, the reference metal electrode 400 may be formed at the inner side of the oxygen ion conductor 100 and the reference metal electrode 400 may be formed at a lower end or a side of the oxygen ion conductor 100.

Further, as the measurement metal electrode 300 and the reference metal electrode 400, platinum (Pt) may be used and the measurement metal electrode 300 and the reference metal electrode 400 are each connected to the voltage measurement wires 600 and the voltage measurement wires 600 are configured to be connected to a separate voltage measurement apparatus E to measure a voltage of a hydrogen measurement sensor 1000 according to the exemplary embodiment of the present invention.

Here, the measurement metal electrode 300 is a contact portion with aluminum or magnesium molten metal (molten metal) and the reference metal electrode 400 contacts air 500. In this case, the hydrogen measurement sensor 1000 generally has a structure in which a conductive material such as porous carbon blocks an middle portion between the aluminum or magnesium molten metal and the measurement metal electrode 300 so as to prevent the aluminum or magnesium molten metal from directly contacting the measurement metal electrode 300, thereby passing through electrons for measuring a voltage and blocking the molten metal.

Further, the hydrogen measurement sensor 1000 according to the exemplary embodiment of the present invention may be configured to further include a ceramic tube 700 which is coupled with an upper portion of the hydrogen ion conductor 200 and has both sides opened. That is, as illustrated in FIG. 3, the ceramic tube 700 has an inside hollowed and both sides opened and thus a lower end thereof is coupled with the upper portion of the hydrogen ion conductor 200 to be lengthily formed in a height direction.

Therefore, the hydrogen measurement sensor 1000 is put into the aluminum or magnesium molten metal and an opened portion of an upper end of the ceramic tube 700 is positioned in the air to measure the content of hydrogen within molten metal 800.

In this case, the upper end of the ceramic tube 700 is formed to be opened and therefore the insides of the ceramic tube 700 and the oxygen ion conductor 100 are introduced with air in the atmosphere and are fully filled with the air 500. Further, the reference metal electrode 400 is connected to voltage measurement wires 610 and 600 and is thus connected to the separate voltage measurement apparatus E and the measurement metal electrode 300 is connected to voltage measurement wires 620 and 600 through the molten metal 800. That is, electricity is conducted to the molten metal 800 and therefore the voltage measurement wires 620 and 600 may be configured to have one portion connected to the voltage measurement apparatus E and the other portion put into the molten metal.

Further, as illustrated in FIG. 4, the hydrogen ion conductor 200 may be formed to be buried into the oxygen ion conductor 100. In this case, the hydrogen ion conductor 200 may be coupled with the oxygen ion conductor 100 so that one portion of the ceramic tube 700 is inserted into the outer side of the oxygen ion conductor 100. Further, as the ceramic tube 700, an alumina tube may be used.

Further, a cover of a porous material such as graphite may be coupled with the outer side of the measurement metal electrode 300, in which the cover may be electrically conducted while preventing a loss of the measurement metal electrode 300 to make hydrogen gas freely be input and discharged and therefore may act as a physical filter.

Hereinafter, a principle of the hydrogen measurement sensor configured as described above will be described.

First, the hydrogen measurement sensor according to the exemplary embodiment of the present invention is configured to largely include the oxygen ion conductor 100, the hydrogen ion conductor 200, the measurement metal electrode 300, and the reference metal electrode 400 and is applied with a principle of an electrochemical hydrogen sensor. The hydrogen measurement sensor 1000 according to the exemplary embodiment of the present invention having the above structure may be shown by a Galvanic cell structure which is represented by the following Equation (1).

$$\text{air}, O_2, Pt | O^{2-} | H^+ | Pt, H_2, \text{melt} \tag{1}$$

In the above Equation (1), the air is air 500, the melt is the molten metal 800, and a chemical reaction contributing to a voltage is as the following Equation (2).

$$H_2 + \tfrac{1}{2}O_2 = H_2O \tag{2}$$

In the above Equation (2), the $H_2$ is the hydrogen partial pressure of the molten metal, the oxygen is the oxygen partial pressure (0.21 atm) in the air, and it may be assumed that the $H_2O$ is constant as a vapor partial pressure at the junction of the hydrogen ion conductor and the oxygen ion conductor. Therefore, the voltage of the above Equation (1) may be represented by the following Equation (3) based on the relationship of $\Delta G = -2FE$.

$$E = -\frac{\Delta G^0}{2F} - \frac{RT}{2F} \ln \frac{p_{H_2O}}{p_{H_2} p_{O_2}^{1/2}} \tag{3}$$

In the above Equation (3), the E is a voltage, the $\Delta G0$ is a difference of standard free energy of the above Equation (2), the F is a Faraday constant, R is a gas constant, $P_{H2}$ is the hydrogen partial pressure of the molten metal, $P_{O2}$ corresponds to 0.21 as the oxygen partial pressure in the air, and the $P_{H2O}$ has a predetermined constant value. Therefore, we may calculate the hydrogen partial pressure by measuring a voltage value E at a temperature T of the molten metal and therefore may understand the concentration of hydrogen existing within the molten metal from a solubility curve corresponding to the hydrogen partial pressure.

Figure 5:
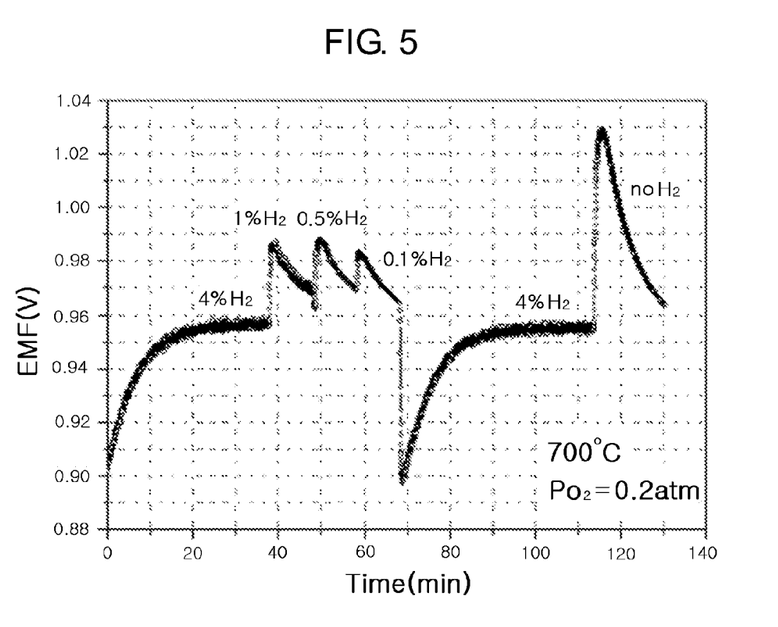
FIG. 5 is a graph illustrating response characteristics of a sensor depending on a concentration of hydrogen gas.

FIG. 5 is a graph measuring voltage characteristics of the sensor by dipping the hydrogen measurement sensor 1000 according to the exemplary embodiment of the present invention in the aluminum molten metal and blowing the specific concentration of hydrogen into the molten metal. In this case, it may be confirmed that the reference metal electrode 400 side uses the oxygen partial pressure in the air and as illustrated, when the concentration of hydrogen is changed, the voltage value is changed well in response to the change.

As such, the hydrogen measurement sensor according to the exemplary embodiment of the present invention may have the same effect as the gas reference material by replacing the reference material of the standard gas method which is difficult to handle with the external air which is easy to handle and therefore the measurement apparatus may be simple.

Further, the hydrogen gas barrel is not required and thus the costs may be saved and the safety may be improved.

In addition, the content of hydrogen within the molten metal may be accurately measured and thus the quality of the final aluminum or magnesium product may be improved and the high reproducibility may be made in the manufacturing process.

The present invention is not limited to the above-mentioned exemplary embodiments but may be variously applied, and may be variously modified by those skilled in the art to which the present invention pertains without departing from the gist of the present invention claimed in the claims.

The invention claimed is:

1. A hydrogen measurement sensor having a junction structure of a solid oxygen ion conductor and a solid hydrogen ion conductor in molten metal, comprising:
    an oxygen ion conductor whose inside is hollow and one portion is open;
    a hydrogen ion conductor coupled with an outer side of the oxygen ion conductor;
    a measurement metal electrode formed at an outer side of the hydrogen ion conductor;
    a reference metal electrode formed inside the oxygen ion conductor; and
    voltage measurement wires connected to the measurement metal electrode and the reference metal electrode, respectively.

2. The hydrogen measurement sensor of claim 1, wherein the oxygen ion conductor is made of a solid electrolyte including zirconia $ZrO_2$ or a solid electrolyte in which $GdO_3$ is added to $CeO_2$-based materials.

3. The hydrogen measurement sensor of claim 2, wherein the zirconia $ZrO_2$ is any one selected from the group consisting of yttria stabilized zirconia (YSZ), calcium stabilized zirconia (CSZ), and magnesium stabilized zirconia (MSZ).

4. The hydrogen measurement sensor of claim 3, further comprising: a ceramic tube which is closed by being coupled to the oxygen ion conductor or the hydrogen ion conductor at a lower end thereof and opened at an upper end thereof.

5. The hydrogen measurement sensor of claim 2, further comprising: a ceramic tube which is closed by being coupled to the oxygen ion conductor or the hydrogen ion conductor at a lower end thereof and opened at an upper end thereof.

6. The hydrogen measurement sensor of claim 1, wherein the hydrogen ion conductor is a compound in which other materials are substituted into place B of a material having an $ABO_3$ type perovskite structure, the compound being selected from the group consisting of $CaZrO_3$-based compounds, $SrZrO_3$-based compounds, $SrCeO_3$-based compounds, $BaCeO_3$-based compounds, $BaTiO_3$-based compounds, $SrTiO_3$-based compounds, and $PbTiO_3$-based compounds.

7. The hydrogen measurement sensor of claim 6, further comprising: a ceramic tube which is closed by being coupled to the oxygen ion conductor or the hydrogen ion conductor at a lower end thereof and opened at an upper end thereof.

8. The hydrogen measurement sensor of claim 1, further comprising: a ceramic tube which is closed by being coupled to the oxygen ion conductor or the hydrogen ion conductor at a lower end thereof and opened at an upper end thereof.

* * * * *